United States Patent [19]

Mistry et al.

[11] Patent Number: 6,123,924
[45] Date of Patent: Sep. 26, 2000

[54] PRESSURIZED AEROSOL INHALATION COMPOSITIONS

[75] Inventors: Suresh N Mistry, Birstall; Mark Gibson, Shepshed, both of United Kingdom

[73] Assignee: Fisons plc, Suffolk, United Kingdom

[21] Appl. No.: 08/478,338

[22] Filed: Jun. 7, 1995

Related U.S. Application Data

[63] Continuation of application No. 08/211,229, Aug. 3, 1994, abandoned, which is a continuation of application No. PCT/GB92/01749, Sep. 23, 1992.

[30] Foreign Application Priority Data

| Sep. 25, 1991 | [GB] | United Kingdom | 9120396 |
| Sep. 28, 1991 | [GB] | United Kingdom | 9120675 |
| Nov. 19, 1991 | [GB] | United Kingdom | 9124661 |
| Feb. 14, 1992 | [GB] | United Kingdom | 9203212 |

[51] Int. Cl.$^7$ .................................................. A61K 9/12
[52] U.S. Cl. ................................ 424/45; 424/43; 424/46; 514/937
[58] Field of Search ........................... 424/45, 46, 43; 252/305; 514/937

[56] References Cited

U.S. PATENT DOCUMENTS

| 4,025,635 | 5/1977 | Hodson et al. | |
| 4,752,466 | 6/1988 | Saferstein et al. | |
| 4,869,899 | 9/1989 | Burghart et al. | |
| 5,225,183 | 7/1993 | Pusewal et al. | 424/45 |
| 5,605,674 | 2/1997 | Pusewal et al. | 424/45 |
| 5,658,549 | 8/1997 | Akehurst et al. | 424/45 |

FOREIGN PATENT DOCUMENTS

| 8705211 | 9/1987 | European Pat. Off. . |
| 0372777 | 6/1990 | European Pat. Off. . |
| 423695 | 4/1991 | European Pat. Off. . |
| 528270 | 5/1972 | Switzerland . |
| 86/01405 | 3/1986 | WIPO . |
| 87/05210 | 9/1987 | WIPO . |
| 87/05211 | 9/1987 | WIPO . |
| 8705210 | 9/1987 | WIPO . |
| 04011 | 4/1991 | WIPO . |
| 91/11173 | 8/1991 | WIPO . |

OTHER PUBLICATIONS

WO,A,8 705 211 ; Sep. 11, 1987; see the whole document.

*Primary Examiner*—James M. Spear
*Attorney, Agent, or Firm*—Nixon & Vanderhye

[57] ABSTRACT

Pressurized aerosol inhalation composition consisting essentially of a liquefied hydrofluoroalkane, a powdered medicament dispersible to form a suspension in the liquefied hydrofluoroalkane, and polyvinylpyrrolidone present in a concentration of 0.00001 to 10% w/w.

16 Claims, No Drawings

PRESSURIZED AEROSOL INHALATION COMPOSITIONS

This is a Rule 62 continuation of application Ser. No. 08/211,229, filed Aug. 3, 1994, now abandoned, and a continuation of PCT/GB92/01749 filed Sep. 23, 1992.

This invention relates to pressurised aerosol compositions, in particular compositions of inhalation medicaments.

BACKGROUND OF THE INVENTION

Pressurised aerosols for the administration of medicaments, and indeed for other applications, conventionally contain one or more liquefied chlorofluorocarbons (CFC's) as propellant. Such materials are suitable for use in such applications since they have the right vapour pressures (or can be mixed in the right proportions to achieve a vapour pressure in the right range) and are essentially taste- and odour-free.

In recent years there has been increasing concern about the depletion of the ozone layer in the upper atmosphere. This is believed to be due to the release into the atmosphere of CFC's and has led to a search for alternative agents for use in all applications of CFC's. To this end, aerosols for many applications are now pressurised using pressurised gases such as nitrogen or hydrocarbons. However, such propellants are generally not suitable for use in the administration of inhalation medicaments since they are toxic and/or the pressure within the canister falls each time the device is used which leads to unreproducible dosing.

The use of hydrofluorocarbons as aerosol propellants has also been suggested. However, considerable difficulties have been encountered in finding suspending agents which are soluble in hydrofluoroalkanes and capable of stabilising medicament suspensions.

DESCRIPTION OF THE INVENTION

Surprisingly, we have found that certain polymers are both soluble in the aerosol propellants and capable of stabilising medicament compositions.

Thus, according to the invention, we provide a pressurised aerosol composition comprising a liquefied hydrofluoroalkane, a powdered medicament dispersable therein and a polymer soluble in the liquefied hydrofluoroalkane, characterised in that the polymer includes recurring structural units, the units being selected from amide containing units and carboxylic acid ester containing units.

The polymer may be a homopolymer, that is the polymer consists of the same recurring structural units, or it may be a copolymer, that is the polymer contains recurring units in addition to either amide containing units or carboxylic acid ester units. The polymer may also be a copolymer of amide containing units and carboxylic acid ester units. Such copolymers may be either block copolymers or random copolymers.

We prefer polymers which include recurring structural units containing an amide group. We particularly prefer the amide containing unit to be 1-ethylene-pyrrolidin-2-one. We especially prefer the polymer to be a homopolymer containing recurring 1-ethylene-pyrrolidin-2-one, that is polyvinylpyrrolidone.

In general, we have found that polyvinylpyrrolidones having a wide range of average molecular weights give acceptable suspensions. Although polymers can be characterised by their weight average molecular weights, viscosity average molecular weights or number average molecular weights, it is more usual to characterise polymers, in particular polymers such as polyvinylpyrrolidone, by K values, in which K is determined from viscosity measurements using the Fikentscher equation (H. Fikentscher, *Cellusochemie*, 1932, 13, 58–64 and 71–74). In particular we prefer the polymer to have a K value of from 10 to 150, more preferably 15 to 120; Particular K values and ranges that may be mentioned include 10–14, 15–18, 29–32, 88–100 and 115–125.

Suitable polymers containing carboxylic acid ester containing recurring structural units include polyvinylacetate and copolymers of vinyl acetate and vinyl pyrrolidone, that is polyvinylpyrrolidone/vinyl acetate copolymer. We have found that polyvinylacetate with a weight average molecular weight of 250,000 gives particularly stable suspensions.

Other polymers that may be mentioned include acrylic acid/methacrylic acid ester copolymers, especially those in which the methyl and ethyl ester groups have been replaced with a low content of trimethylammomiumethyl groups, preferably at a ratio of 1:20, especially at a ratio of 1:40. We have found that such copolymers having a weight average molecular weight of 150,000 give stable suspensions.

The amount of polymer in the composition will depend on the active ingredient to be dispersed, its concentration and the particular polymer selected. However, in general the amount of polymer is from 0.00001 to 10% w/w, more preferably 0.001 to 5% w/w and especially 0.001 to 1% w/w.

The compositions may, in addition to the polymer, contain other excipients, in particular excipients intended to improve valve lubrication and excipients to modify flavour. Particular lubricants that may be mentioned include polyethoxylated compounds, especially polyethylene glycol. We prefer polyethylene glycol having a mean molecular weight of from 200 to 3000, preferably 400 to 2000, eg 1500. Other polyethoxylated compounds that may be used as lubricants include polysorbates, eg polysorbate 80, and alkyl aryl polyether alcohols, eg tyloxapol. Other lubricating excipients that may be mentioned include high molecular weight fully halogenated chlorofluorocarbons and esters of medium chain fatty acids. The amount of lubricant in the composition will depend on the other components of the composition, the active ingredient, the nature of the valve, etc. In general, we prefer a concentration of 0.01 to 4% w/w and more preferably 0.1 to 2% w/w.

Flavour modifying excipients that may be added to the composition include peppermint oil, menthol, Dentomint (Dentomint is a tradename), saccharin and saccharin sodium. When the flavour modifying excipient is a solid, preferably it is micronised. The concentration will depend on the individual composition and the flavour modifying excipient. In general, we prefer a concentration of 0.005 to 4% w/w; more preferably 0.01 to 1% w/w.

By the term 'hydrofluoroalkane' we mean a compound of general formula $$C_xH_yF_z$$

in which x is an integer from 1 to 3, y+z=2x+2 and y and z are both at least 1.

Particular hydrofluoroalkanes of interest are $CF_3CFH_2$ (Propelant 134a), $CH_3CHF_2$ (Propellant 152a) and $CF_3CHFCF_3$ (Propellant 227). We particularly prefer compositions including propellant 227.

In general the vapour pressure of the propellant mixture should be in the range suitable and permitted for aerosol propellants. The vapour pressure may be varied by mixing one or more hydrofluoroalkanes and/or some other suitable vapour pressure modifying agent in appropriate proportions.

We prefer the vapour pressure of the mixture to be in the range 20 to 100 psig, more preferably 40 to 80 psig, eg about 60 psig.

In certain case we have found it advantageous to add to the compositions excipients capable of increasing the solubility of the polymer or of other excipients, in the propellant. In general we have found that the polymers selected have a solubility in the propellant of at least 0.0001% w/w, preferably at least 0.001% w/w, particularly 0.01% w/w and especially 0.1% w/w. Excipients capable of increasing the solubility of the polymer include liquid excipients which are more polar than the liquefied propellant, where polarity is defined in terms of relative Kauri butanol values, as described in European patent application 0 372 777. Particular excipients that may be mentioned include alcohols eg ethanol and isopropanol. However, in contrast to the teaching of EP 0 373 777, we have found that only very small quantities of such excipients are required. In particular we have found that good compositions can be prepared in propellant 134a with a polyvinylpyrolidone as polymer with a variety of active ingredients and less than 10% w/w, preferably less than 5% w/w, more preferably less than 2% w/w, eg 0.2% w/w ethanol.

Medicaments which may be dispersed in the propellant mixture according to the invention include any medicaments which are conventionally administered to the lung and/or nose by inhalation of a pressurised aerosol formulation. Such medicaments include drugs for use in the prophylactic or remedial treatment of reversible obstructive airways disease, eg drugs such as sodium cromoglycate, nedocromil sodium, inhaled steroids, eg beclomethasone dipropionate, fluticasone propionate, budesonide and tipredane, and bronchodilators, eg salbutamol, reproterol, terbutaline, formoterol, pirbuterol, isoprenaline, salmeterol, fenoterol and salts thereof, ad anticholinergic agents such as ipratropium bromide, oxitropium bromide and atropine and combinations of two or more of these agents, eg a combination of a prophylactic agent with a bronchodilator, eg sodium cromoglycate with salbutamol.

Other medicaments that may be mentioned include antihistamines, eg clemastine, pentamidine and salts thereof, acetyl-β-methylcholine bromide, peptide hormones such as insulin and amylin, bradykinin antagonists, $PLA_2$ inhibitors, PAF antagonists, lipoxygenase inhibitors, leukotriene antagonists, CNS active drugs, such as NMDA antagonists, glutamate antagonists, CCK agonists and antagonists; macrolide compounds including FK 506, rapamycin, cyclosporin and structurally related compounds, vitamins, vaccines, eg MMR vaccine and polio vaccine and vectors for gene therapy, eg plasmids containing genes intended to correct genetic disorders such as cystic fibrosis.

Where the medicament is intended for delivery to the lung, it preferably has a particle size distribution such that a high proportion of the particles are of a size capable of penetrating deep into the lung. In particular, the medicament is preferably in a form having a mass median diameter of from 0.01 to 10 μm, more preferably from 0.1 to 4 μm, eg about 2 or 3 μm.

The amount of medicament in the composition will depend on the nature of the active ingredient and the condition to be treated. However, the composition preferably comprises from 0.01 to 15% w/w, preferably from 0.1 to 10% w/w, and most preferably from 0.5 to 5% w/w medicament.

According to a further aspect of the invention there is provided a method of producing a pressurised aerosol composition as herein described, which comprises dispersing the powdered medicament and the polymer in the liquefied hydrofluoroalkane.

In particular, the compositions may be produced by cold fill or pressure fill techniques. In cold filling, the ingredients are placed in a cooled mixing vessel, cooled liquefied propellant added and a dispersion produced by vigorous stirring. Alternatively, a slurry may be prepared of the ingredients in a portion of cooled liquid propellant and the remainder of the liquefied propellant added under vigorous stirring. Aliquots of the dispersed composition are then filed into cooled aerosol cans and sealed with a suitable valve, eg a metering valve.

In pressure filling, the ingredients are placed in a pressure vessel, liquefied propellant added under pressure through a valve and a dispersion of the ingredients in the liquefied dispersed composition are then filled, under pressure, through the valve into suitable cans provided with appropriate valves, eg metering valves.

The compositions according to the invention are advantageous in that the solubility of the polymer is such as to ensure good dispersion of the medicament and smooth operation of the aerosol valve.

The compositions of the present invention may also be advantageous in that they are substantially taste- and odour-free and have suitable vapour pressures for the administration of medicaments by inhalation, yet are environmentally safe and acceptable, especially when compare with compositions including chlorofluorocarbons. In addition, they may be less irritant than corresponding compositions including conventional surfactants such as oleic acid and sorbitan trioleate.

The performance of the compositions according to the present invention can be assessed using the following test procedures:

1. Settling times

A glass bottle containing the composition is gently shaken five times and then stood upright. The time interval between standing the bottle upright and the first appearance of flocculation or separation of powder in the propellant determined ($S_1$). Timing is continued until complete separation, defined as when three lines of standard newspaper print can be read through the propellant from the top or bottom, depending on whether the active ingredient floats or sinks ($S_2$). In some compositions, complete separation does not occur. For these compositions, a turbidity factor ranging from 1 to 5 is determined, 1 denoting that a small proportion of the active ingredient is suspended and 5 denoting that the majority of the active ingredient is suspended.

2. Dispersion Tests

Dispersion testing on compositions formulated in cans having a metering valve can be assessed using a glass multistage liquid impinger, eg of the type described by J. H. Bell et al, *J. Pharm. Sci.*, 1971, 60(10), 1559.

3. Lubrication

The lubricating effects of the composition can be assessed by filling the formulation into a can and closing the can with a modified metering valve from which the return spring has been removed. The stem of the valve is subjected to a compression force and the reading recorded in Newtons. This gives a measure of the lubricating efficacy of the composition.

4. Dose uniformity

Dose uniformity is assessed by discharging a metered dose aerosol can containing the composition into a filter tube which has sufficient air flowing through it to entrain all the dose. The tube is washed out with a suitable solvent and the amount of medicament assayed. The medicament entrained on the mouthpiece is also washed off and assayed. The variation of dose evaluated throughout the life of the can is a measure of dose uniformity. In a variation of this test, dose uniformity after standing can be assessed by shaking the aerosol can, allowing to stand for a predetermined time and assessing dose in the manner described above.

5. Caking potential

Compositions to be assessed are filled into plastic coated glass bottles. The assessment is carried out by allowing the samples to be stored for a period of time in order that complete sedimentation and compaction of the powder mass can take place, eg 3 months. After that period, the glass bottles are shaken by gentle twisting of the hand to totally invert the bottles. The number of bottle inversions required to completely resuspend the drug is noted. The number gives a measure of the degree of compaction of the composition. Since ease of drug particle redispersion is essential for dose uniformity, any composition requiring more tan 5 shakes suggests possible problems in long-term storage.

The invention will now be illustrated, but in no way limited, by the following Examples.

EXAMPLES

Method

The required amounts of micronised active ingredient, suspending agent and other excipients, were weighed into plastic coated glass bottles and crimped with an appropriate valve. The desired amount of liquefied propellant was then transferred using a transfer button and the contents of the bottle sonicated to ensure thorough mixing. Unless otherwise stated, the fill volume for the bottles was 20 ml.

Materials

Active ingredients

All active ingredients were micronised. In general, the active ingredients were anhydrous, although nedocromil sodium and sodium cromoglycate were used in their equilibrium hydrated form which each contain about 10% w/w water at room temperature.

Polyethyleneglycols (PEG)

The average molecular weight of the polyethyleneglycol used is indicated by the number 200, 400, etc following PEG.

Halocarbon oil

Halocarbon oil is the proprietary name given to a series of high molecular weight fully halogenated chlorofluorocarbons of chlorotrifluoroethylene telomers obtainable from Halocarbon Products Corporation, New Jersey, USA.

Miglyols

Miglyol® neutral oils

Miglyol® neutral oils are esters of medium chain fatty acids and are sometimes referred to as fractionated coconut oils. Miglyol is a trademark of Hüls AG. The following oils were used.

Miglyol®810

A triglyceride of fractionated $C_8/C_{10}$ coconut oil fatty acids classified by the CTFA as caprylic/capric triglyceride. It meets the requirements of the British Pharmacopoeia 1988 for the monograph "Fractionated Coconut Oil". It is a low viscosity of oil of neutral taste and smell, with a turbidity point below 0° C.

Miglyol® 829

A glyceryl ester of fractionated $C_8/C_{10}$ coconut fatty acids linked to succinic acid and is classified by the CTFA as caprylic/capric/diglyceryl succinate. It has a turbidity point below −20° C., is soluble in alcohol, has a viscosity of approximately 250 mPa.s and a density of approximately 1.

Miglyol® 840

A propylene glycol diester of saturated vegetable fatty acids with $C_8/C_{10}$ chain lengths, classified by the CFTA as propyleneglycol dicaprylate/dicaprate. It meets the requirements of the German Pharmacopoeia, DAR9, 1st supplement, for the monograph "Propyleneglycolcoctanoato-decanoate". It has a turbidity point below −30° C. and is soluble in 90% ethanol.

Polyvinylpyrrolidones

All polyvinylpyrrolidones used were essentially linear homopolymers formed by the free radical polymerisation of N-vinylpyrrolidone. PVP(K29/31), PVP(K90), PVP(K120), PVP(C15) and PVP(C30) refer to the polyvinylpyrrolidones obtainable from GAF Chemical Corporation and sold under the Trade Mark PLASDONE®. PVP/17PF refers to KOLLIDON 17PF, a polyvinylpyrrolidone available from BASF (KOLLIDON is a registered Trade Mark).

The manufacturing processes for polyvinylpyrrolidone and the other polymers used herein produce polymer mixtures containing molecules of unequal chain length and thus different molecular weights. Such polymers are usually characterised by their K values, in which K is determined from viscosity measurements using the Fikentscher equation (H. Fikentscher, *Cellusochemie*, 1932, 13, 58–64 and 71–74). The polymers can also be characterised by their average molecular weights ($\overline{M}w$), viscosity average molecular weights ($\overline{M}v$) and number average molecular weights ($\overline{M}n$).

Characterising data for the polyvinylpyrrolidones used were as follows:

|  | K | $\overline{M}w$ | $\overline{M}v$ | $\overline{M}n$ |
| --- | --- | --- | --- | --- |
| PVP 17 PF | 15 – 18 | 9000 | — | 2500 |
| K29/32 | 29 – 32 | — | — | — |
| K90 | 94 ± 6 | 1,280,000 | 63000 | — |
| K120 | 120 ± 5 | 2,800,000 | 1,450,000 | — |
| C15 | 17 ± 1 | 10500 | 7000 | 3000 |
| C30 | 30.5 ± 1 | 62500 | 3800 | 16500 |

Polyvinylpyrrolidone/vinylacetate copolymers

Polyvinylpyrrolidone/vinylacetate copolymers are obtainable from GAF Chemical Corporation. The E- and I- series of PVP/VA copolymers were supplied as 50% solutions in ethanol and isopropanol respectively. S-630 refers to the white, spray dried polymer of PVP/VA having the characteristics set out below. Characterising data for PVP/VA used:

|  |  | K value | VP/VA ratio |
| --- | --- | --- | --- |
| PVP/VA | S-630 | 30–50 | 60/40 |
|  | E-535 | 30–50 | 50/50 |
|  | 1-535 | 25–35 | 50/50 |
|  | E-335 | 25–35 | 30/70 |

Acrylic acid/methacrylic acid ester copolymers

The acrylic acid/methacrylic acid ester copolymers used were copolymers synthesized from acrylic and methacrylic acid ethyl and methyl esters with a low content of quaternary ammonium groups. The molar ratio of these ammonium groups to the neutral (meth)acrylic acid esters if 1:40. The weight average molecular weight is approximately 150000. the polymer used was EUDRAGIT RS PM, obtainable from Röhn Pharma GmbH. (EUDRAGIT is a registered Trade Mark).

Polyvinylacetate

The polyvinylacetate used had a weight average molecular weight of about 26,000.

A. Compositions containing polyvinylpyrrolidone and propellant 227

The following active ingredients were formulated at the concentration shown with PVP in propellant 227 PLASDONE C30 (PLASDONE is a registered Trade Mark of GAF Chemicals Corporation).

| a) | | with 0.05% w/w PVP(C-30) | |
|---|---|---|---|
| | 1. | Terbutaline sulphate | 5 mg/ml |
| | 2. | Beclomethasone dipropionate | 5 mg/ml |
| | 3. | Salbutamol sulphate | 4 mg/ml |
| | 4. | Fluticasone propionate | 4 mg/ml |
| | 5. | Reproterol hydrochloride | 10 mg/ml |
| | 6. | Fenoterol hydrobromide | 4 mg/ml |
| | 7. | Sodium cromoglycate | 10 mg/ml |
| | 8. | Sodium cromoglycate | 50 mg/ml |
| | 9. | Ipratropium bromide | 0.8 mg/ml |
| | 10. | Pentamidine isoethionate | 4 mg/ml |
| | 11. | Clemastine | 4 mg/ml |
| | 12. | Acetyl-β-methylcholine bromide | 10 mg/ml |
| | 13. | Budesonide | 4 mg/ml |
| b) | | with 0.1% w/v PVP(17PF) | |
| | 1. | Fenoterol hydrobromide | 4 mg/ml |
| | 2. | Terbutaline sulphate | 5 mg/ml |
| | 3. | Salbutamol sulphate | 4 mg/ml |
| c) | | with 0.025% w/v PVP(C30) | |
| | 1. | Tipredane | 10 mg/ml |

B. Compositions containing polyvinylpryyolidone/vinyl acetate copolymer in propellant 227

The following active ingredients were formulated in propellant 227 at the concentrations shown.

| a) | | with 0.05% w/v PVP/VA S-630 | |
|---|---|---|---|
| | 1. | Terbutaline sulphate | 5 mg/ml |
| | 2. | Beclomethasone dipropionate | 5 mg/ml |
| | 3. | Salbutamol sulphate | 4 mg/ml |
| | 4. | Fluticasone propionate | 4 mg/ml |
| | 5. | Reproterol hydrochloride | 10 mg/ml |
| | 6. | Fenoterol hydrobromide | 4 mg/ml |
| | 7. | Sodium cromoglycate | 10 mg/ml |
| | 8. | Sodium cromoglycate | 50 mg/ml |
| | 9. | Ipratropium bromide | 0.8 mg/ml |
| | 10. | Acetyl-β-methylcholine bromide | 10 mg/ml |
| | 11. | Budesonide | 4 mg/ml |
| b) | | with 0.025% w/v PVP/VA S-630 | |
| | 1. | Tipredane | 10 mg/ml |

C. Compositions containing PVP or PVP/VA, propellant 227 and polyethylene glycol The following active ingredients were formulated in propellant 227 at the concentration shown with 0.5% w/v PEG600.

| a) | | with 0.05% w/v PVP(C30) | |
|---|---|---|---|
| | 1. | Salbutamol sulphate | 4 mg/ml |
| | 2. | Sodium cromoglycate | 50 mg/ml |
| | 3. | Reproterol hydrochloride | 10 mg/ml |

-continued

| b) | | with 0.5% w/v PVP/VA S-630 | |
|---|---|---|---|
| | 1. | Salbutamol sulphate | 4 mg/ml |
| | 2. | Sodium cromoglycate | 50 mg/ml |
| | 3. | Reproterol hydrochloride | 10 mg/ml |
| | 4. | Budesonide | 4 mg/ml |
| c) | | with 0.1% w/v PVP(17PF) | |
| | 1. | Terbutaline sulphate | 5 mg/ml |
| | 2. | Fenoterol hydrobromide | 4 mg/ml |

D. Compositions containing acrylic acid/methacrylic acid ester copolymers and propellant 227

The following active ingredients were formulated at the concentration shown with 0.1% w/v EUDRAGIT RS (EUDRAGIT is a Trade Mark of Röhn Pharma GmbH) in propellant 227.

| a) | 1. | Terbutaline | 5 mg/ml |
|---|---|---|---|
| | 2. | Beclomethasone dipropionate | 5 mg/ml |
| | 3. | Salbutamol sulphate | 4 mg/ml |
| | 4. | Fluticasone | 4 mg/ml |
| | 5. | Reproterol hydrochloride | 10 mg/ml |
| | 6. | Fenoterol | 4 mg/ml |
| | 7. | Sodium cromoglycate | 10 mg/ml |
| | 8. | Ipratropium bromide | 0.8 mg/ml |
| | 9. | Clemastine | 4 mg/ml |
| | 10. | Acetyl-β-methylcholine bromide | 10 mg/ml |
| b) | compositions including 0.5% w/w PEG 600 | | |
| | 11. | Beclomethasone dipropionate | 5 mg/ml |
| | 12. | Sodium cromoglycate | 50 mg/ml |
| | 13. | Reproterol hydrochloride | 10 mg/ml |
| | 14. | Fenoterol hydrobromide | 4 mg/ml |

E. Compositions in propellant 134a

The following active ingredients were formulated at the concentration shown in propellant 134a.

| 1. | Tipredane | 10 mg/ml |
|---|---|---|
| | PVP(C30) | 0.1% w/w |
| | ethanol | 5.0% w/w |
| 2. | Tipredane | 10 mg/ml |
| | PVP(C30) | 0.1% w/w |
| | ethanol | 10.0% w/w |
| 3. | Nedocromil sodium | 20 mg/ml |
| | PVP(C30) | 0.1% w/w |
| | ethanol | 5.0% w/w |
| 4. | Nedocromil sodium | 20 mg/ml |
| | PVP(C30) | 0.1% w/w |
| | ethanol | 10.0% w/w |
| 5. | Tipredane | 10 mg/ml |
| | PVP/VA S-630 | 0.1% w/w |
| | ethanol | 5.0% w/w |
| 6. | Tipredane | 10 mg/ml |
| | PVP(C30) | 0.25% w/w |
| | ethanol | 5.0% w/w |
| 7. | Tipredane | 10 mg/ml |
| | PVP(C30) | 0.5% w/w |
| | ethanol | 5.0% w/w |
| 8. | Nedocromil sodium | 20 mg/ml |
| | PVP/VA S-630 | 0.1% w/w |
| | ethanol | 5.0% w/w |
| 9. | Nedocromil sodium | 20 mg/ml |
| | PVP/C30 | 0.25% w/w |
| | ethanol | 5.0% w/w |
| 10. | Nedocromil sodium | 20 mg/ml |
| | PVP(C30) | 0.5% w/w |
| | ethanol | 5.0% w/w |
| 11. | Tipredane | 10 mg/ml |

|     |                      |             |
| --- | -------------------- | ----------- |
|     | PVP(C30)             | 0.1% w/w    |
|     | PEG 600              | 0.5% w/w    |
|     | ethanol              | 5.0% w/w    |
| 12. | Tipredane            | 10 mg/ml    |
|     | PVP(C30)             | 0.1% w/w    |
|     | PEG 600              | 0.5% w/w    |
|     | ethanol              | 10.0% w/w   |
| 13. | Nedocromil sodium    | 20 mg/ml    |
|     | PVP(C30)             | 0.1% w/w    |
|     | PEG 600              | 0.5% w/w    |
|     | ethanol              | 5.0% w/w    |
| 14. | Nedocromil sodium    | 20 mg/ml    |
|     | PVP(C30)             | 0.1% w/w    |
|     | PEG 600              | 0.5% w/w    |
|     | ethanol              | 10.0% w/w   |
| 15. | Nedocromil sodium    | 20 mg/ml    |
|     | PVP(C30)             | 0.05% w/w   |
|     | PEG 600              | 0.5% w/w    |
|     | ethanol              | 0.2% w/w    |
| 16. | Beclomethasone dipropionate | 5 mg/ml |
|     | PVP/VA S-630         | 0.1% w/w    |
|     | ethanol              | 2.0% w/w    |
| 17. | Beclomethasone dipropionate | 5 mg/ml |
|     | PVP/VA S-630         | 0.1% w/w    |
|     | ethanol              | 5.0% w/w    |
| 18. | Beclomethasone dipropionate | 5 mg/ml |
|     | PVP(C30)             | 0.1% w/w    |
|     | ethanol              | 5.0% w/w    |

F. Compositions containing polyvinylacetate

|     |                   |             |
| --- | ----------------- | ----------- |
| a)  | in propellant 134a |            |
| 1.  | Tipredane         | 10 mg/ml    |
|     | Polyvinylacetate  | 0.042% w/w  |
| 2.  | Nedocromil sodium | 20 mg/ml    |
|     | Polyvinylacetate  | 0.042% w/w  |
| b)  | in propellant 227 |             |
| 1.  | Tipredane         | 10 mg/ml    |
|     | Polyvinylacetate  | 0.035% w/w  |
| 2.  | Nedocromil sodium | 20 mg/ml    |
|     | Polyvinylacetate  | 0.035% w/w  |

G. Compositions using polyvinylpyrrolidone of different K values

The following active ingredients were formulated in propellant 227 at the concentrations shown, with 0.1% w/w polyvinylpyrrolidone having the K value shown:

|     |                          |          |
| --- | ------------------------ | -------- |
| a)  | PVP(K29/32)              |          |
| 1.  | Tipredane                | 10 mg/ml |
| 2.  | Nedocromil sodium        | 20 mg/ml |
| 3.  | Sodium cromoglycate      | 20 mg/ml |
| 4.  | Reproterol hydrochloride | 4 mg/ml  |
| 5.  | Salbutamol sulphate      | 4 mg/ml  |
| b)  | PVP(K90)                 |          |
| 1.  | Tipredane                | 10 mg/ml |
| 2.  | Nedocromil sodium        | 20 mg/ml |
| c)  | PVP(K120)                |          |
| 1.  | Tipredane                | 10 mg/ml |
| 2.  | Nedocromil sodium        | 20 mg/ml |
| d)  | PVP(C15)                 |          |
| 1.  | Tipredane                | 10 mg/ml |
| 2.  | Nedocromil sodium        | 20 mg/ml |

H. Compositions using polyvinylpyrrolidone/vinylacetate copolymers of different vinylpyrrolidone/vinylacetate ratios Tipredane and nedocromil sodium were formulated in propellant 227 at the concentrations shown, with 0.1% w/w PVP/VA having the vinylpyrrolidone/vinylacetate ratio shown.

|     |                      |            |         |
| --- | -------------------- | ---------- | ------- |
| a)  | Nedocromil sodium 20 mg/ml |      |         |
|     | 1.                   | PVP/VA E-535 | (50/50) |
|     | 2.                   | PVP/VA I-535 | (50/50) |
|     | 3.                   | PVP/VA E-335 | (30/70) |
| b)  | Tipredane 10 mg/ml   |            |         |
|     | 1.                   | PVP/VA E-535 | (50/50) |
|     | 2.                   | PVP/VA I-535 | (50/50) |
|     | 3.                   | PVP/VA E-335 | (30/70) |

I. Further tipredane formulations

| Ex | Tipredane (mg/ml) | PVP/VA S-630 % w/w | PVP/C30 % w/w | Propellant |
| --- | --- | --- | --- | --- |
| 1  | 4  | 0.0025 | —      | 134a |
| 2  | 4  | 0.01   | —      | 134a |
| 3  | 4  | 0.025  | —      | 134a |
| 4  | 4  | 0.05   | —      | 134a |
| 5  | 10 | 0.0025 | —      | 134a |
| 6  | 10 | 0.01   | —      | 134a |
| 7  | 10 | 0.025  | —      | 134a |
| 8  | 10 | 0.05   | —      | 134a |
| 9  | 30 | 0.0025 | —      | 134a |
| 10 | 30 | 0.01   | —      | 134a |
| 11 | 30 | 0.025  | —      | 134a |
| 12 | 30 | 0.05   | —      | 134a |
| 13 | 4  | 0.0025 | —      | 227  |
| 14 | 4  | 0.01   | —      | 227  |
| 15 | 4  | 0.025  | —      | 227  |
| 16 | 4  | 0.05   | —      | 227  |
| 17 | 10 | 0.0025 | —      | 227  |
| 18 | 10 | 0.01   | —      | 227  |
| 19 | 10 | 0.025  | —      | 227  |
| 20 | 10 | 0.05   | —      | 227  |
| 21 | 30 | 0.0025 | —      | 227  |
| 22 | 30 | 0.01   | —      | 227  |
| 23 | 30 | 0.025  | —      | 227  |
| 24 | 30 | 0.05   | —      | 227  |
| 25 | 4  | —      | 0.0025 | 134a |
| 26 | 4  | —      | 0.01   | 134a |
| 27 | 4  | —      | 0.025  | 134a |
| 28 | 4  | —      | 0.05   | 134a |
| 29 | 10 | —      | 0.0025 | 134a |
| 30 | 10 | —      | 0.01   | 134a |
| 31 | 10 | —      | 0.025  | 134a |
| 32 | 10 | —      | 0.05   | 134a |
| 33 | 30 | —      | 0.0025 | 134a |
| 34 | 30 | —      | 0.01   | 134a |
| 35 | 30 | —      | 0.025  | 134a |
| 36 | 30 | —      | 0.05   | 134a |
| 37 | 4  | —      | 0.0025 | 227  |
| 38 | 4  | —      | 0.01   | 227  |
| 39 | 4  | —      | 0.025  | 227  |
| 40 | 4  | —      | 0.05   | 227  |
| 41 | 10 | —      | 0.0025 | 227  |
| 42 | 10 | —      | 0.01   | 227  |

-continued

| Ex | Tipredane (mg/ml) | PVP/VA S-630 % w/w | PVP/C30 % w/w | Propellant |
|----|----|----|----|----|
| 43 | 10 | — | 0.025 | 227 |
| 44 | 10 | — | 0.05 | 227 |
| 45 | 30 | — | 0.0025 | 227 |
| 46 | 30 | — | 0.01 | 227 |
| 47 | 30 | — | 0.025 | 227 |
| 48 | 30 | — | 0.05 | 227 |

J. Compositions containing flavouring agents

The following compositions were made up in propellant 227, with 0.1% w/w PVP/VA S-630.

| 1. | Nedocromil sodium | 20 mg/ml |
|----|----|----|
|    | peppermint oil | 0.1% w/w |
| 2. | Nedocromil sodium | 20 mg/ml |
|    | menthol | 0.05% w/w |
|    | saccharin | 0.03% w/w |
| 3. | Tipredane | 10 mg/ml |
|    | menthol | 0.05% w/w |
|    | saccharin | 0.03% w/w |

K. Compositions containing additional excipients

The following composition was made up in propellant 227, to examine the effects of different excipients as valve lubricants.

| a) | Nedocromil sodium | 20 mg/ml |
|----|----|----|
|    | PVP/C30 | 0.1% w/w |
|    | Lubricant | 0.5% w/w |
|    | Menthol | 0.05% w/w |
|    | Saccharin, micronised | 0.03% w/w |
|    | Lubricants: | |
|    | PEG 200 | |
|    | PEG 400 | |
|    | PEG 600 | |
|    | PEG 1000 | |
|    | Miglyol 810 | |
|    | Miglyol 829 | |
|    | Miglyol 840 | |
|    | Ethyl oleate | |
|    | Halocarbon oil 27 | |
|    | Tyloxapol | |
|    | Polysorbate 80 | |
| b) | Nedocromil sodium | 20 mg/ml |
|    | PVP (C30) | 0.10% w/w |
|    | PEG 1500 | 0.20% w/w |
|    | Menthol | 0.05% w/w |
|    | Saccharin, micronised | 0.03% w/w |
| c) | Tipredane | 10.0 mg/ml |
|    | PVP (C30) | 0.10% w/w |
|    | Lubricant | 0.50% w/w |
|    | Lubricants: PEG 600 | |
|    | PEG 1000 | |
| d) | Tipredane | 10.0 mg/ml |
|    | PVP (C30) | 0.10% w/w |
|    | Lubricant | 0.20% w/w |
|    | Lubricants: PEG 600 | |
|    | PEG 1000 | |
|    | PEG 1500 | |

What is claimed is:

1. A pressurized aerosol inhalation composition consisting essentially of:

a liquefied hydrofluoroalkane;

a powdered medicament dispersible to form a suspension in the liquefied hydrofluoroalkane; and polyvinylpyrrolidone present in a concentration of 0.00001 to 10% w/w.

2. A composition according to claim 1, wherein the medicament is selected from the group consisting of one or more of terbutaline sulphate, beclomethasone dipropionate, salbutamol sulphate, fluticasone pripionate, reproterol hydrochloride, fenoterol hydrobromide, sodium cromoglycate, nedocromil sodium, tipredane, pentamidine isoethionate, clemastine, acetyl-β-methylcholine bromide and budesonide.

3. A process for the preparation of a composition according to claim 1, which comprises dispersing the powdered medicament and the polyvinylpyrrolidone in the liquefied hydrofluoroalkane.

4. A composition according to claim 1, wherein the powdered medicament has a mass median diameter of 0.01 to 10 μm.

5. A composition according to claim 1, wherein the powdered medicament has a mass median diameter of 0.001 to 4 μm.

6. A composition according to claim 1, wherein the hydrofluoroalkane is $CF_3CHFCF_3$.

7. A composition according to claim 1, wherein the concentration of medicament is from 0.01 to 15% w/w.

8. A composition according to claim 1, which contains an excipient which acts as a valve lubricant.

9. A composition according to claim 1, which contains a flavor modifying excipient.

10. A composition according to claim 1, which contains an excipient which acts as a valve lubricant and a flavor modifying excipient.

11. A composition according to claim 8, wherein the excipient comprises polyethylene glycol.

12. A composition according to claim 11, wherein the polyethylene glycol has a mean molecular weight of from 200 to 3000.

13. A composition according to claim 12, wherein the polyethylene glycol has a mean molecular weight of from 40 to 2000.

14. A composition according to claim 11, wherein the excipient is present at a concentration of between 0.01 to 4% w/w.

15. A composition according to claim 11, wherein the excipient is present at a concentration of between 0.1 to 2% w/w.

16. A composition according to claim 9, wherein the flavor modifying excipient is selected from the group consisting of peppermint oil, menthol, saccharin or saccharin sodium.

* * * * *